(12) United States Patent
Kim (10) Patent No.: US 11,065,200 B2
(45) Date of Patent: Jul. 20, 2021

(54) MUCOADHESIVE DEVICES FOR THE RELEASE OF PROBIOTICS AND FOR THE MAINTENANCE OF THEIR ENZYME ACTIVITIES

(71) Applicant: MENDES S.R.L., Ardea (IT)

(72) Inventor: Seok-Jin Kim, Seoul (KR)

(73) Assignee: MENDES S.R.L., Ardea (IT)

( * ) Notice: Subject to any disclaimer, the term of this patent is extended or adjusted under 35 U.S.C. 154(b) by 0 days.

(21) Appl. No.: 16/494,148

(22) PCT Filed: Mar. 14, 2018

(86) PCT No.: PCT/KR2018/002968
§ 371 (c)(1),
(2) Date: Sep. 13, 2019

(87) PCT Pub. No.: WO2018/169296
PCT Pub. Date: Sep. 20, 2018

(65) Prior Publication Data
US 2020/0078294 A1    Mar. 12, 2020

(30) Foreign Application Priority Data
Mar. 15, 2017  (KR) .................. 10-2017-0032382

(51) Int. Cl.
| | | |
|---|---|---|
| *A61K 9/00* | (2006.01) |
| *A61K 8/02* | (2006.01) |
| *A61K 8/66* | (2006.01) |
| *A61K 8/99* | (2017.01) |
| *A61K 35/745* | (2015.01) |
| *A61K 35/747* | (2015.01) |
| *A61K 38/50* | (2006.01) |
| *A61Q 19/00* | (2006.01) |

(52) U.S. Cl.
CPC ............ *A61K 9/006* (2013.01); *A61K 8/0216* (2013.01); *A61K 8/66* (2013.01); *A61K 8/99* (2013.01); *A61K 35/745* (2013.01); *A61K 35/747* (2013.01); *A61K 38/50* (2013.01); *A61Q 19/00* (2013.01)

(58) Field of Classification Search
None
See application file for complete search history.

(56) References Cited

U.S. PATENT DOCUMENTS 6,962,697 B2 * 11/2005 Cavaliere widow Vesely ............
    C12Y 301/04012
    424/93.45
2005/0057210 A1  3/2005 Ueda et al.
2018/0133210 A1  5/2018 Finn et al.

FOREIGN PATENT DOCUMENTS

JP    2010132653 A  *  6/2010
JP    2010132653 A     10/2010

OTHER PUBLICATIONS

Doron et al. 2015 (Risk and Safety of Probiotics; CID 2015:60 (Suppl 2), S129). (Year: 2015).*
Smealty et al., "Formulation and Evaluation of Mucoadhesive buccal films of enalapril maleate" Indian Journal of Pharmaceutical Sciences, 2010, v 72, n. 5, p. 571-575.

* cited by examiner

*Primary Examiner* — Mary Maille Lyons
(74) *Attorney, Agent, or Firm* — Greer, Burns & Crain, LTD.; Gregory P. Einhorn (57) ABSTRACT

The present invention relates to medical devices in the form of mucoadhesive films for the release of live lactic bacteria and bifidobacteria (probiotics) and/or for the release and maintenance of their pharmacologically useful enzyme activities.

27 Claims, 4 Drawing Sheets

MUCOADHESIVE DEVICES FOR THE RELEASE OF PROBIOTICS AND FOR THE MAINTENANCE OF THEIR ENZYME ACTIVITIES

RELATED APPLICATIONS

This application is a U.S. national phase patent application claiming benefit of priority to PCT International patent application number PCT/KR2018/002968, filed Mar. 14, 2018, which claims priority to Korean Patent application no. 10-2017-0032382, filed Mar. 15, 2017. The aforementioned applications are expressly incorporated herein by reference in its entirety and for all purposes.

TECHNICAL FIELD

The present invention relates to mucoadhesive devices for application to the mucosa for the release of live probiotic bacteria and/or their enzymes. In particular the present invention relates to medical devices in the form of mucoadhesive buccal films, where the buccal mucosa is a good predictive model for the results which would be obtained in the treatment of other mucosa through the release of *Lactobacillus brevis* ATCC 4006 and/or through the release and maintenance of their pharmacologically useful enzyme activities.

BACKGROUND ART

Dental plaque is a biofilm and is the main component of the bacterial ecosystem (microbiota) present in the oral cavity. The bacterial species making up this microbiota are very many in number, of the order of several thousands, and of these it is estimated that approximately a thousand go to make up the biofilm surrounding the teeth.

According to investigators, the oral microbiota forms a part of the defence system for the buccal environment, preventing colonisation of the mouth by pathogenic bacteria. It is very likely that this defensive function explains its relative stability over time, despite the environmental changes regularly occurring (Marsh and Brandshaw, 1995; Kolenbrander and Palmer, 2004).

It follows that the occurrence of an imbalance in the composition of the dental biofilm can give rise to the appearance of dental caries, periodontal problems and halitosis (Badet and Thebaud, 2008). For example, dental caries are characterised by the growth of Streptococci belonging to the mutans group (Selwiz et al., 2007). Periodontal problems, on the other hand, of which for example we will cite periodontitis, are associated with the growth of bacterial species such as *Porphyromonas gingivalis, Treponema denticola, Tannerella forsythia* and *Aggregatibacter actinomycetecomitans* which are capable of circumventing the host's defences and colonising sites under the gum, causing tissue damage (Houle et al., 2003; Offenbacher, 1996). Chemotherapy and radiotherapy can quite frequently give rise to oral mucositis, which comprises the rapid death of cells in the most superficial layers of the buccal mucosa, with the appearance of very painful inflammation and ulceration that becomes an easy target for bacterial and viral infections. The effects of oral mucositis can seriously compromise individuals' quality of life, limiting their ability to feed themselves (Naidu et al., 2004).

Lactic bacteria are gram-positive bacteria characterised by the ability to derive the energy needed for their own survival from the process of the fermentation of hexose sugars to lactic acid, or lactic acid and ethanol. At the present time, the genera *Lactobacillus, Leuconostoc, Pediococcus, Streptococcus* and *Lactococcus* are classified as lactic bacteria. Other bacteria that produce lactic acid from sugars, although via a different metabolic route, are the bifidobacteria. Lactic bacteria and bifidobacteria are included in the group of bacteria known as "probiotics", which have a number of beneficial actions, above all, but not only, in the intestines of mammals and in particular in humans.

Lactic bacteria and bifidobacteria secrete a number of antimicrobial substances, such as organic acids, hydrogen peroxide and bacteriocins and compete with buccal pathogens for adhesion sites on the mucosa (Reid et al., 2003; Meurman, 2005). Thus the use of lactic bacteria and bifidobacteria to overcome the pathological effects of disturbances among the micro-organisms in the oral cavity, is a promising alternative treatment for the treatment of human beings and animals, in addition to being an effective method of caring for personal hygiene through maintaining proper dental health and health of the oral cavity. In fact lactic bacteria and bifidobacteria are capable of compromising the vitality of pathogenic microorganisms through modulating the pH and/or oxidation-reduction potential of the environment in which they live, stimulating non-specific immune mechanisms and modulating humoural and cellular immune response (Erickson et al., 2000; Marco et al., 2006).

The bacterial strain *Lactobacillus brevis* ATCC 4006 is capable of producing large quantities of arginine deiminases and sphingomyelinases. In particular the prokaryotic enzyme arginine deiminase is typical of this bacterium (Di Marzio et al., 2001) and is responsible for the breakdown of arginine. Through the activity of this enzyme the bacterial strain *Lactobacillus brevis* ATCC 4006 causes arginine, which is a precursor of polyamine synthesis, influencing the growth of tumour cells in vitro (Di Marzio et al., 2001), to be removed from the environment. Because eukaryotic cells also use arginine to produce nitric oxide (NO), an important mediator of the inflammatory process, removal of the precursor arginine from the cellular environment can significantly reduce the production of NO and thus modulate the inflammatory response. Bacterial sphingomyelinase is an enzyme capable of hydrolysing PAF (Platelet Activating Factor), a potent inflammatory cytokine (Rui-Dong Duan, 2006).

The efficacy of this probiotic in diseases which also involve an inflammatory process in the mucosa is probably to be accounted for by this enzyme activity. In addition to applications in the field of dentistry, for example, for the treatment of mucositis, aphthous stomatitis, and dental caries, lactic bacteria in general and *Lactobacillus brevis* ATCC 4006 in particular may for example also be used in the case of vaginitis and vaginosis, procto-haemorrhoidal inflammations, forms of sinusitis, otitis and conjunctivitis, gastritis and oesophagitis.

It has recently been demonstrated that *Lactobacillus brevis* ATCC 4006 can have beneficial effects in the treatment of some oral diseases. This probiotic is currently marketed in a tablet formulation for dissolution in the mouth, under the name Inersan®.

Della Riccia et al. (Della Riccia et al., 2007) have evaluated the anti-inflammatory effects of this formulation of *Lactobacillus brevis* ATCC 4006 in a group of patients suffering from chronic periodontitis, with positive effect. In addition to this, *L. brevis* has proved to be a promising agent for preventing formation of the buccal biofilm caused by *Prevotella melaninogenica*, one of the causal agents of periodontitis (Vuotto et al., 2013).

Piyush Shah et al. (2013) have compared the oral administration of Inersan® and Doxycycline alone with the combination Inersan® and antibiotiin a sample of patients suffering from periodontitis and Inersan® and Doxycycline alone vs. the combination of Inersan® and antibiotic in a sample of patients suffering from aggressive periodontitis and proved that the probiotic has a favourable action on gingival inflammation, the appearance of caries, and the presence of Lactobacilli in the buccal environment. The efficacy of tablets containing *Lactobacillus brevis* ATCC 4006 has also been demonstrated in the treatment of oral ulcers in patients suffering from Behcet's Syndrome (Tasli et al., 2006). Recently, in a double-blind randomised study with control against placebo it has been shown that lozenges containing *L. brevis* ATCC 4006 have a positive action on reducing bleeding from the gums, on the generation of acids by plaque and the number of undesired bacteria in the oral cavity (Campus et al., 2013).

Toiviainen, A. et al. (2014) describe the use of a lozenge formulation of Lacto*bacillus rhamnosus* GG and *Bifidobacterium animalis* subsp. *lactis* BB-12 for the short-term (4 week) treatment of gingival inflammation and plaque in healthy patients. This study has confirmed the activity of the bacterial strains used on reducing plaque and gingival inflammation.

The ever increasing frequency of resistance to antibiotics phenomena has caused an increase in interest in probiotic bacteria, which, like *Lactobacillus brevis* ATCC 4006, are capable of acting against the occurrence of problems in the oral cavity. In addition to this, in the oncological field, an effective and non-toxic treatment of mucosal conditions can greatly increase the compliance of individuals undergoing chemotherapy treatment.

It is therefore of fundamental importance to find effective means of administering lactic bacteria and bifidobacteria which prolong release times, prolong their presence at sites of action, and maintain the enzyme activities expressed by the said probiotics.

The choice of a suitable delivery system is therefore essential for efficacy of treatment of the mucosa in general, and the oral cavity in particular, through the use of lactic bacteria and bifidobacteria.

Mucoadhesion is the adhesion of a natural or synthetic polymer or a dosage vehicle comprising this to mucosa. This phenomenon may be used for pharmaceutical delivery and is particularly useful for mucosal treatment, and in particular buccal treatment with probiotics, in that it makes it possible to localise release of the bacteria and the beneficial substances which they produce.

In general mucoadhesive materials comprise hydrophilic macromolecules containing a large number of groups capable of forming hydrogen bonds, in particular hydroxyl or carboxyl groups. The process of mucoadhesion includes the formation of very close and intimate contact between the surface of the mucosa, in particular the mucin covering it, and the polymer chains of the material comprising the mucoadhesive system. This intimate contact is essentially based on the formation of secondary crosslinking bonds, in particular hydrogen bonds. The possibility of modulating the release of a drug and adhesion of a dosage form to the mucosa needs to be evaluated on the basis of individual pharmaceutical applications. For a review relating to the mechanisms underlying mucoadhesion see Smart, J. D. (2005) and Yadav, V. K. et al., 2010. Examples of mucoadhesive systems for buccal use are described in Abruzzo et al., 2012 and Salamat-Miller et al., 2005.

The film form of dosage (Oral Thin Film; OTF) is particularly suitable for use in the oral cavity, thanks to properties such as thinness of the film and its ease of application (Peh and Wong, 1999). An OTF with a suitably designed formulation can adhere to the oral mucosa, slowly dissolving in contact with saliva. In addition to this the film can be applied directly to the surface of lesions when required by the disease, allowing better treatment of the problem.

The production of mucoadhesive films is commonly carried out by "casting" (Siemann, U., 2005). For an exhaustive review of materials which can be used to produce delivery systems based on mucoadhesion see Yadav, V. K. et al., above.

Those skilled in the art are aware of the particular complexity of mucoadhesive delivery, which can be influenced by many factors, such as the properties of the polymer (s) used, the concentration of mucoadhesive polymer present, the flexibility of the polymer chains used, their spatial conformation in relation to environmental factors such as pH, initial contact time, and the swelling ability of the polymer(s) used. In addition to this many physiological factors, such as replacement of the mucin molecules present on the surface of the mucosa being treated and the physical-chemical condition of the mucosa during the course of a disease, also contribute to the optimum success of mucoadhesive delivery (Yadav, V. K. et al., above). In addition to the factors described above, as far as the delivery of lactic bacteria and bifidobacteria to the oral cavity is concerned, it is of fundamental importance that the said bacteria are as far as possible kept vital during the course of preparation of the mucoadhesive formulation and during the period of storage preceding its use, that they be released at the site of action, efficiently and in a living form, and finally, that their useful enzyme activities are preserved.

The buccal mucoadhesive delivery of lactic bacteria and bifidobacteria has hitherto received little study, hence the interest in using these bacteria for local oral treatment is very recent. Data on the utility of some probiotics in the prevention and treatment of problems within the oral cavity have in fact only been available for a short time.

Recently, Saha, S. et al. (Saha, S. et al., 2013) have described OTF containing carboxymethylcellulose (CMC) at a concentration of between 0.012 and 1% for buccal use. These OTF constituted a vehicle for the lactic bacterium *Lactobacillus fermentum* NCIB 5221. The procedure described by these authors provides for the preparation of a solution of CMC in twice-distilled water, to which the desired quantity of bacteria originating from a fresh culture centrifuged and re-suspended in 0.85% w/v saline solution is added. Subsequently the films were dried at ambient temperature for 12 hours under a laminar flow of air and kept sealed in Petri dishes at ambient temperature. The OTF so obtained showed a considerable loss of vitality in the probiotic during the production procedure (of the order of two orders of magnitude), to the point of containing approximately $6.75 \times 10^8$ bacteria in a film 100 mm (10 cm) in diameter. A further loss of vitality was observed in storage (approximately one order of magnitude), and ultimately living probiotic was completely absent after 150 days storage at ambient temperature. Another specific aspect lies in the high dissolution rate of these films, of the order of 4 minutes, which could be an obstacle if it is desired to modulate release of the probiotic at the site of action. In fact, release of the probiotic in vitro reached a maximum peak after approximately 5 minutes.

Heinemann et al. (Heinemann et al., 2013) formulated "orally-disintegratinfilms" as a vehicle fo *Lactobacillus acidophilus* or *Bifidobacterium animalis* subsp. *Lactis*. W. These strains were loaded into films comprising carboxymethylcellulose, gelatin and starch. Again, in this case, the procedure described provided for the preparation of a polymer solution to which the desired quantity of bacteria originating from a fresh culture centrifuged and re-suspended in 0.9% w/v saline solution was added. The drying stage was instead carried out at 30° C. for 24 hours in a ventilated stove. In the study the counts showed a loss of probiotics of less than 15% after the film preparation procedure, but the vitality of the probiotics fell drastically after 90 days storage.

On the basis of all this there was therefore felt a need to develop mucoadhesive films with innovative characteristics in comparison with the films described in the literature.

DISCLOSURE OF INVENTION

Technical Problem

The present invention relates to medical devices in the form of mucoadhesive films for the release of live lactic bacteria and bifidobacteria (probiotics) and/or for the release and maintenance of their pharmacologically useful enzyme activities.

Solution to Problem

The object of the present invention comprises the preparation of mucoadhesive films containing at least one bacterial strain, in which:

a) the beneficial enzyme activities present in at least one bacterium and *bifidobacterium* are preserved over a long period, and b) release of at least one bacterium and *bifidobacterium* in vivo is localised and significantly prolonged over time.

These films have optimum characteristics in terms of maintaining the vitality of the preselected bacterial strains and the beneficial enzyme activities present in them during the stages of processing and storage, and in terms of the in vivo release of living bacteria at the site of action.

Another object of the present invention are buccal mucoadhesive films in which the particularly preferred lactic bacterium is *Lactobacillus brevis* ATCC 4006 and the particularly preferred mucoadhesive polymer is hydroxypropylmethylcellulose (HPMC). Other preferred lactic bacteria and bifidobacteria are *Lactobacillus salivarius* DSM 24800, *Lactobacillus plantarum* DSM 24801, *Streptococcus thermophilus* DSM 24731, *Lactobacillus acidophilus* DSM 24735, *Lactobacillus delbrueckii* ssp *bulgaricus* DSM 24734, *Lactobacillus paracasei* DSM 24733, *Lactobacillus plantarum* DSM 24730, *Bifidobacterium longum* DSM 24736, *Bifidobacterium infantis* DSM 24727, *Bifidobacterium breve* DSM 24732 and corresponding mixtures thereof and mixtures with ATCC 4006.

Another object of the invention is a method for preparing the said mucoadhesive films containing at least one bacterial strain selected from lactic bacteria and bifidobacteria and their corresponding enzyme activities. The at least particularly preferred bacterial strain is *Lactobacillus brevis* ATCC 4006. Other preferred lactic bacteria and bifidobacteria are *Lactobacillus salivarius* DSM 24800, *Lactobacillus plantarum* DSM 24801, *Streptococcus thermophilus* DSM 24731, *Lactobacillus* acidophilus DSM 24735, *Lactobacillus delbrueckii* ssp *bulgaricus* DSM 24734, Lacto*bacillus paraca-sei* DSM 24733, *Lactobacillus plantarum* DSM 24730, *Bifidobacterium longum* DSM 24736, *Bifidobacterium infantis* DSM 24727, *Bifidobacterium breve* DSM 24732 and mixtures thereof.

Another object of the invention is use of the said mucoadhesive films for the prevention and treatment of disturbances and conditions of the mucosa in animals and man, in particular the oral, genital, anal, nasal, pharyngeal, oesophageal and conjunctival mucosa.

A further object of the present invention is use of the said mucoadhesive films for the treatment of skin disturbances and tumours, for example in the treatment of melanoma, abrasions, open wounds, skin ulcers, sores in general and pressure sores in particular.

Other objects will be apparent from the following detailed description and appended claims.

BRIEF DESCRIPTION OF DRAWINGS

FIG. 1B shows the basal side of the film, which is devoid of bacteria.

FIG. 3: Survival of the lactic bacterium *Lactobacillus brevis* ATCC 4006 in mucosal films during a twelve month storage period (48 weeks) at temperatures of 2 8° C. and 24° C. (ambient temperatur(a) Lot I; (b) Lot II; (c) Lot III. t0=baseline; t1=2 weeks; t2=4 weeks; t3=8 weeks; t4=12 weeks; t5=24 weeks; t6=36 weeks; t7=48 weeks.

FIG. 4: Progress in enzyme activity in mucosal films during a twelve month storage period (48 weeks) at a temperature of 2-8° C. and 24° C. (ambient temperatur(a) Lot I; (b) Lot II; (c) Lot III. t0=baseline; t4=12 weeks; t5=24 weeks; t6=36 weeks; t7=48 weeks.

MODE FOR THE INVENTION

In this text and for the purpose of the present invention the terms "Mucoadhesive OTF(s)" (Oral Thin Film; OTF) and "mucoadhesive film(s)" are to be regarded as being synonymous, and therefore their use is also intended for all types of mucosa other than the oral mucosa. In the rest of this text and for the purposes of the present invention the term "probiotic" and "probiotics" means at least one bacterial strain selected from the lactic bacteria and bifidobacteria as defined above, and mixtures thereof.

The Inventors have unexpectedly found a method of preparation which makes it possible to obtain mucoadhesive OTF (Oral Thin Film; OTF) containing high quantities of live probiotic, which are capable of maintaining vitality and/or enzyme activity over a long period (up to 12 months and beyond) under suitable environmental conditions. In vivo the mucoadhesive OTF according to the invention enabled prolonged release (at least 10 hours) of vital probiotic into the oral cavity, or into the mucosa in general, following every single application.

Suitable mucoadhesive polymers are described in Yadav, V. K. et al., see above.

Monomers commonly used in the preparation of mucoadhesive films, and therefore known to those skilled in the art, are for example: hydroxyethyl methacrylate (HEMA); hydroxyethoxyethyl methacrylate (HEEMA); hydroxydiethoxyethyl methacrylate (HDEEMA); methoxyethyl methacrylate (MEMA); methoxyethoxyethyl methacrylate (MEEMA); methoxydiethoxyethyl methacrylate (MDEEMA); ethylene glycol dimethacrylate (EGDMA); N-vinyl-2-pyrrolidone (NVP); N-isopropyl AAm (NIPAAm); vinyl acetate (VAc); lactic acid (LA); acrylic acid (AA); methacrylic acid (MAA); N-(2-hydroxypropyl) methacrylamide (HPMA); ethylene glycol (EG); propylene glycol (PG); PEG acrylate (PEGA); PEG methacrylate (PEGMA); PEG diacrylate (PEGDA); PEG dimethacrylate (PEGDMA); ethylene oxide (EO); propylene oxide (PO); and combinations thereof in order to obtain mucoadhesive homopolymers and copolymers.

Particularly suitable mucoadhesive polymers are selected from those based on or containing sodium alginate or hyaluronic acid, gelatins and carboxymethylcellulose. Hydroxypropylmethylcellulose is particularly suitable for production of the mucoadhesive films according to the invention.

The mucoadhesive films according to the invention may also be prepared using other known mucoadhesive polymers, for example, polymers containing cellulose or polymers of cellulose, such as for example hydroxymethylcellulose, hydroxyethylcellulose, hydroxypropylcellulose, polymers based on or containing ethylene or propylene oxide, polymers based on or containing beta-glucans, such as pullulan (beta-1,4-; beta-1,6-glucan), polyvinyl pyrrolidone, polyvinyl alcohol, sodium alginate, sodium hyaluronate, polyethylene glycol, gums such as xanthan gum, gum adragant, guar gum, acacia gum, polyacrylic acid, polymers and copolymers of acrylic and methacrylic acid, carboxyvinyl polymers and copolymers, starches, natural and synthetic gelatins, agarose gel, polysaccharides, glucans, xanthans, agarose-xanthan gel, starches, chitosans, dextrans, pectins, cellulose, methyl-, ethyl-, propyl-cellulose; and mixtures and combinations thereof.

Plasticising substances known to those skilled in the art, that is substances which render the final film more flexible, may be added to these polymers, generally in proportions from 0.5 to 30% or preferably from 0.5 to 20% with respect to the weight of the polymer used. Among these plasticising substances we will mention, for example, polyalkylene oxides such as polyethylene glycol and polypropylene glycol, small organic molecules such as glycerol, glycerol monoacetate, glycerol triacetate (also known as triacetin), polysorbate, cetyl alcohol, or sorbitol, taken individually or as mixtures thereof. Among these, the preferred plasticisers are polypropylene glycol and PEG (polyethylene glycol).

Mucoadhesion is based on consolidated technology, and those skilled in the art may select the most appropriate mucoadhesive system for the final use.

The mucoadhesive films according to the invention are prepared by the technology known as "film casting". The film casting method according to the invention incorporates significant variant in comparison with the basic method known to those skilled in the art. This variant comprises preparing a solution of polymer in a solvent, which is typically water, without mixing the probiotic into it, as is instead specified by current practice and described in Saha et al., above. In addition to this, in the variant according to the invention, plasticising agent is preferably added to the aqueous solution of mucoadhesive polymer, which is different from what is described by Saha et al., above.

All stages in production of the mucoadhesive films are preferably carried out in a sterile environment.

The method of preparing the mucoadhesive film according to the invention comprises the stages of:

mixing the mucoadhesive polymer with water (preferred quantity: from 1% w/w to 3% w/w) and plasticiser (preferred quantity: from 0% or from 0.5% to 5% w/w on the basis of the weight of the polymer), dissolution being encouraged by gentle stirring, carried out, for example, over 8 and 12 hours. The viscous solution is then preferably allowed to stand for a further 10-12 hours at ambient temperature to ensure that bubbles disappear;

pouring the mixture so prepared onto a flat surface to achieve a uniform thickness, preferably ≤5 mm. Suitable moulds of desired dimensions may be used and allowed to dry at a temperature of 30° C., preferably 30-60° C., more preferably 45-55° C., typically for 2 hours, preferably for 4-6 hours.

depositing and distributing the probiotic (for example, *Lactobacillus brevis* ATCC 4006) or the preselected enzyme product, for example arginine deiminase or sphingomyelinase, onto the surface of the dehydrated film obtained in the preceding stage, for example by spraying, in the desired concentration per unit surface area and in a pure and dehydrated form, for example, in a lyophilised form or a product dehydrated by spray-drying or other techniques known to those skilled in the art;

then drying the mucoadhesive film obtained during the previous stage until the preparation reaches constant weight. This drying stage is carried out at ambient temperature, preferably under vacuum, in the presence of a dehydrating agent, such as for example silica gel, typically for 18-26 hours, until a suitably dehydrated stable product is obtained.

Figure 1:
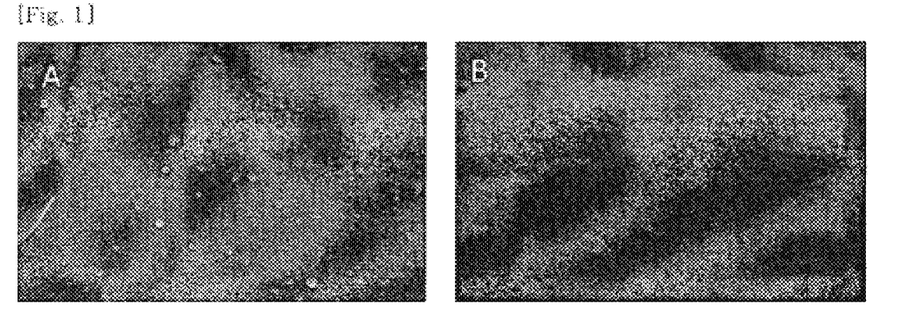
FIG. 1: Image obtained using a scanning electron microscope showing the presence of the lactic bacterium *Lactobacillus brevis* ATCC 4006 only on the side of the mucoadhesive film onto which it has been sprayed in a dehydrated form (FIG. 1A).

The OTF obtained in this way have highly reproducible specifications. They have a thickness of ≤1 mm, preferably ≤500 μm, more preferably ≤100 μm, for example between 80.00 and 90.00 μm, for examp 88.33 μm, and are shaped in such a way that release of the probiotic is one-way, in that it is only present on one side of the film (see FIG. 1). This characteristic, which is not present in known OTF (Saha et al.), makes it possible for the end user to place the probiotic in direct contact with the mucosa or with the external environment (for example the buccal cavity), depending upon therapeutic needs. FIG. 1A demonstrates the uniform distribution of the lactobacilli on the surface of the film sprayed with bacterial lyophilisate.

One particularly advantageous and unexpected characteristic is the quantity of probiotic which can be loaded onto each mucoadhesive film. It is in fact possible to load even $1 \times 10^8$ cfu or more bacteria onto an OTF 1 cm in diameter, typically $1 \times 10^2$-$1 \times 10^{12}$ cfu. This is particularly advantageous in comparison with the buccal mucoadhesive films in the known art, in particular with regard to the work of Saha et al., above. The possibility of loading large quantities of probiotic and prolonged release of the bacteria constitutes an appreciable and unforeseen improvement in comparison with the buccal mucoadhesive films in the known art.

Weight variation between mucoadhesive films within individual lots is very limited and is between 9.0 mg and 9.6 mg.

Like the weight, the thickness of the film also proves to be very reproducible, varying by approximately 5-10%, with low standard deviation values, as shown in Table 1 in the "Examples" section. These data indicate that the production method is capable of providing reproducible uniform films in terms of weight and thickness. The film may be subdivided into units typically having dimensions of 10×10 cm and be packed in a suitable primary packaging for pharmaceutical and non-pharmaceutical use. Each unit can be subsequently cut using an ordinary pair of scissors at the time of application to adjust the dimensions of the film to the part to which the unit is applied, for example the mucosal lesion, in particular in the buccal mucosa. The film may also be prepared in strips and wound to form a tape which can be cut at the time of use. Advantageously the individual portions of film contain a uniform concentration of active ingredient (probiotic and/or enzyme).

Figure 2:
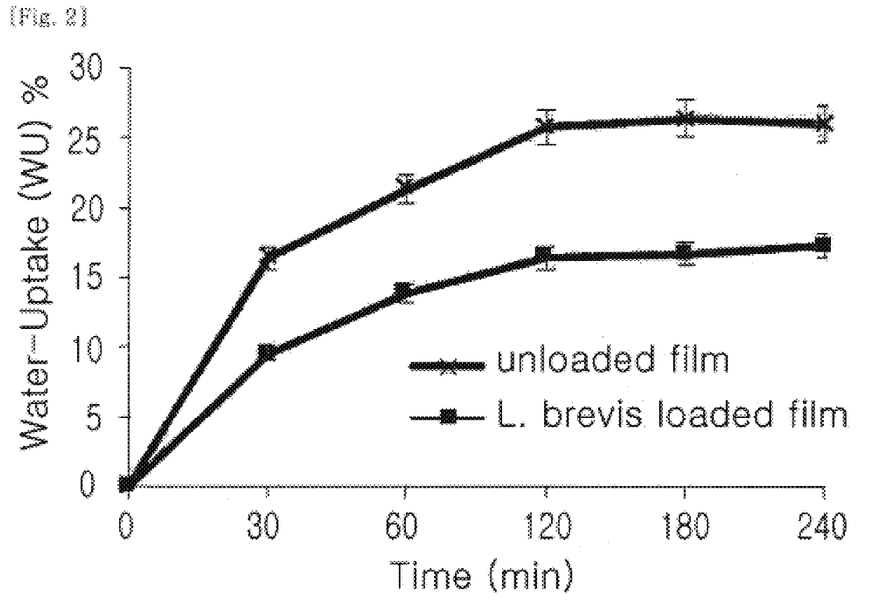
FIG. 2: Results of an in vitro hydration test on mucoadhesive films containing unloaded HPMC or containing the lactic bacterium *Lactobacillus brevis* ATCC 4006. The data for each point refer to five different films in three different lots.

Data relating to the in vitro hydration capacity of OTF according to the invention are shown in FIG. 2 and relate to measurements made on films loaded with probiotic, in comparison with films without probiotic, in the presence of simulated human saliva (for experimental details see the "Examples" section below). Under the experimental conditions used the OTF according to the invention proved to hydrate relatively slowly, with a maximum percentage hydration peak at 120 minutes (2 hours); during this stage the OTF became transformed into a gelled semi-solid system which enabled efficient adhesion to the mucosa and prolonged release over time. This characteristic is an appreciable improvement in comparison with the OTF in the known art. The mucoadhesive films of Saha et al. (above), for example, showed a high dissolution rate (approximately 4 minutes) with a maximum peak release of the probiotic in vitro after approximately 5 minutes.

The mucoadhesive films according to the invention, loaded with probiotic, hydrated with more difficulty than those without probiotic. This characteristic does not however seem to be an obstacle to their in vivo functions, as illustrated below.

The mucoadhesion tests were carried out in vivo on healthy volunteers, as described below in the "Examples" section. None of the volunteers reported any discomfort in the use of OTF according to the invention, and no signs of inflammation or damage to the gingival mucosa after removal of the film from the oral cavity were revealed. The buccal mucosa constitute a good predictive model for the results that can be achieved in the treatment of other mucosa.

Once adhering to the gingival mucosa, the films required approximately 2 hours for complete hydration, and remained adhering for a further 8±2 hours until they were removed or dissolved. Rapid adhesion of the films to the mucosa, without giving rise to the normal feeling of inconvenience due to the presence of a foreign body, also reduced the production of saliva. This property encourages already good permanence of the probiotic and its enzyme products in the buccal cavity and on the mucosa.

Release of the probiotic was studied in vivo on healthy volunteers. The experimental procedure used for these experiments is reported in the "Examples" section below. Tables 3 and 4 show the data obtained by applying the film with the side containing probiotic towards the buccal cavity (Table 3) and with the side containing the probiotic towards the gingival mucosa (Table 4). Samples of saliva were collected before application of the film (t0 h) and after 2 hours (t2 h) and 10 hours (t10 h). The data obtained by applying the film with the probiotic towards the buccal cavity indicate that the mucoadhesive films according to the invention are capable of releasing the probiotic gradually, also appreciably increasing the population of lactobacilli in the oral cavity. The increase in *lactobacillus* concentration was particularly marked in individuals D and E at $t_{10\ h}$, but was also evident in the samples from individuals A and B.

The data relating to the tests on healthy volunteers using mucoadhesive gel with the side containing probiotic towards the gum are shown in Table 4. Again in this case, an increase in the probiotic count was noted in all the volunteers 10 hours after application. This behaviour was more obvious in individuals B and E, in whom the probiotic concentration reached values of 3.61 log CFU and 4.36 log CFU starting from values below the detection limit.

The mucoadhesive films according to the invention also make it possible to preserve useful enzyme activities in the loaded bacteria. Table 5 reported in the "Examples" section shows the results obtained by measuring the presence of citrulline in saliva samples taken as described above after application of the film with probiotic towards the buccal cavity. Citrulline is the end product of the arginine conversion reaction brought about by the enzyme arginine deiminase. These data relate in particular to mucoadhesive films according to the invention containing the probiotic *Lactobacillus brevis* ATCC 4006, a bacterium having appreciable arginine deiminase activity. The quantity of citrulline increased in saliva samples 2 hours after application of the film (except in individual D), demonstrating release of the enzyme from the film. A fall in the quantity of citrulline also appeared to occur 10 minutes after application (except in individual A). The reduction in activities after 10 hours can be explained as a decrease in expression of the enzyme or inhibition of its activity as a result of possible environmental changes after 10 hours of treatment.

The behaviour of the mucoadhesive films according to the invention was also studied during the post-production storage period.

Table 2 in the "Examples" section shows the water content of films stored at +2-8° C. and +24° C. for the periods of time indicated.

It was observed that the water content fell, probably as a result of storage in containers capable of trapping moisture present in the environment. Also, as was predictable, the films stored at +24° C. lost more water than the films stored at +2-8° C. This phenomenon did not however show any macroscopic changes in the characteristics and integrity of the films.

Survival of the probiotic *L. brevis* ATCC 4006 was also studied, again in the three lots of experimental films stored at the same temperatures as described above.

Figure 3A:
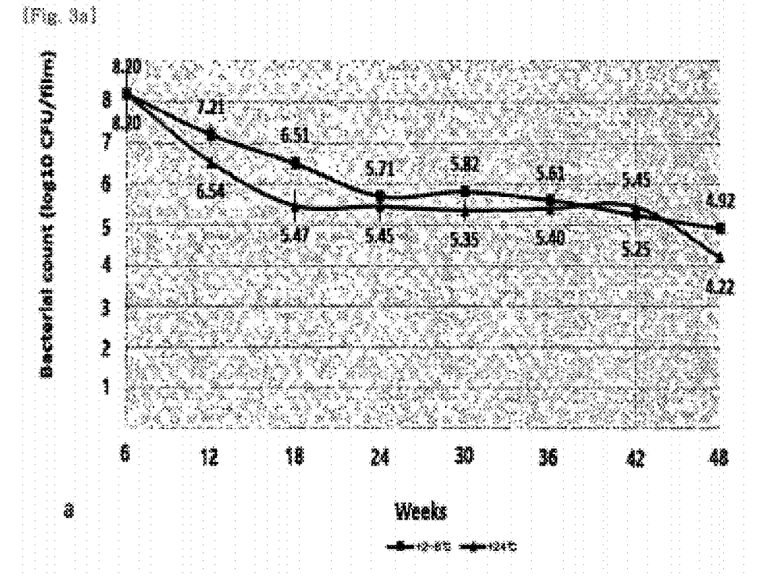
Figure 3B:
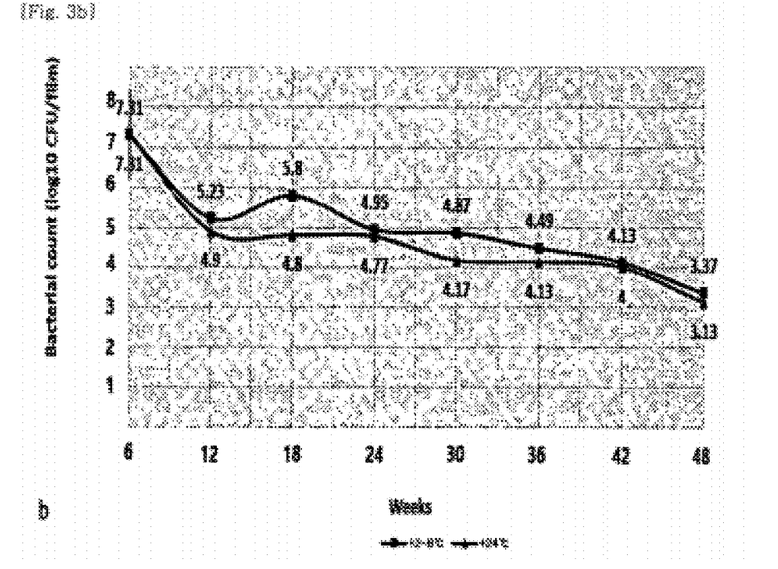
Figure 3C:
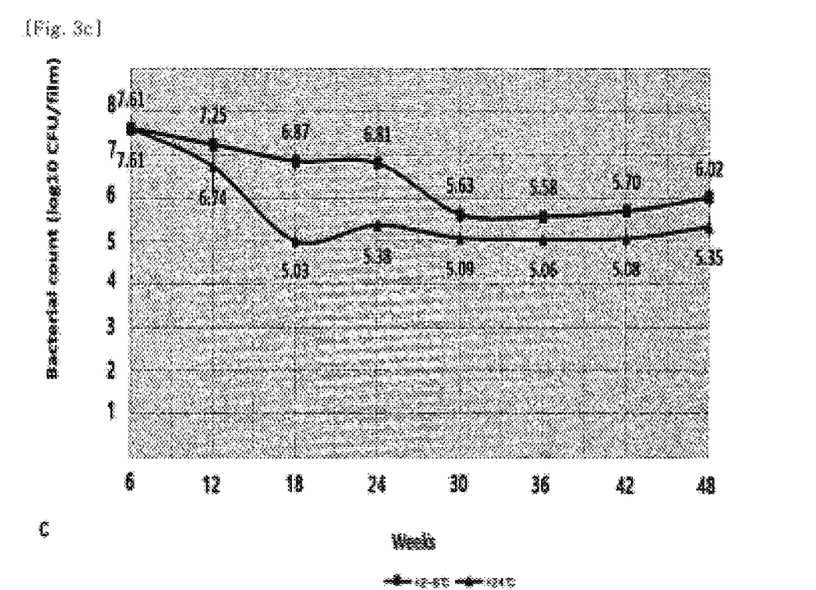

The data shown in FIG. 3 show survival of the probiotic *L. brevis* ATCC 4006 during a storage period of 12 months for three production lots. In Lot I the vital bacterial cells decreased from 8.20 log CFU to 4.92 log CFU when the mucoadhesive OTF were stored at +2-8° C. (losses up to 3.28 log; 60.00% survival) and down to 4.22 log CFU when the films were stored at +24° C. (loss equal to 3.98 log; 51.46% survival). In Lot II the live bacterial cells fell from 7.31 log CFU to 3.37 log CFU (loss equal to 3.94 log; 46.10% survival) at +2-8° C. and 3.13 log CFU at +24° C. (loss equal to 4.18 log; 42.82% survival). In Lot III the living bacterial cells decreased from 7.61 log CFU to 6.02 log CFU (loss equal to 1.59 log; 79.11% survival) at +2-8° C., while they fell to 5.35 log CFU at +24° C. (loss equal to 2.26 log; 70.30% survival).

The mean survival for the probiotic *L. brevis* ATCC 4006 in buccal films stored at +2-8° C. was 61.74%, while for those stored at +24° C. it was 54.86%.

Persistence of enzyme activity of the enzyme arginine deiminase was also assessed, again in the three lots of experimental films stored at the same temperature as described above.

Figure 4A:
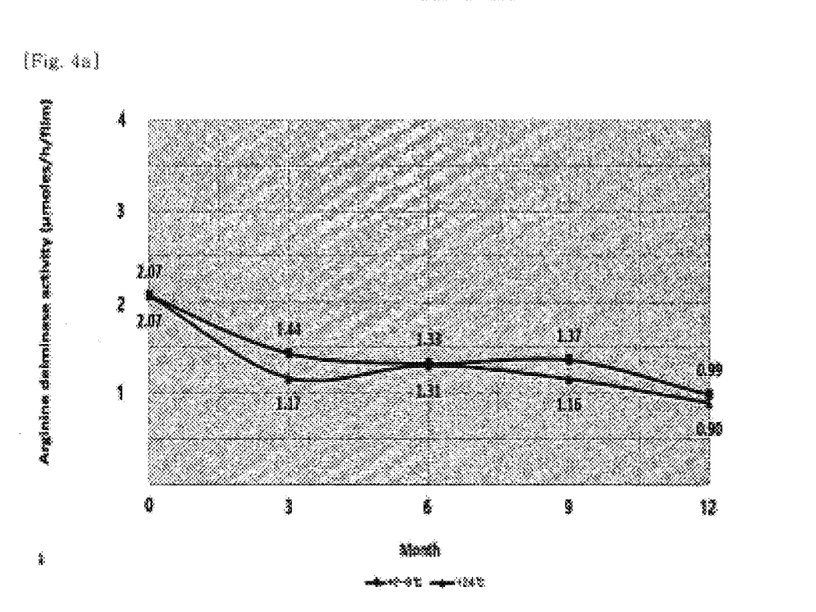
Figure 4B:
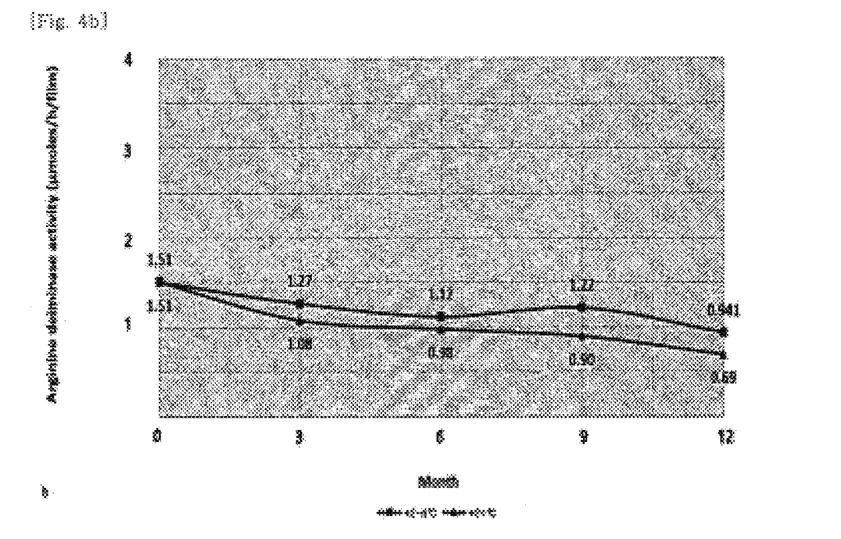
Figure 4C:
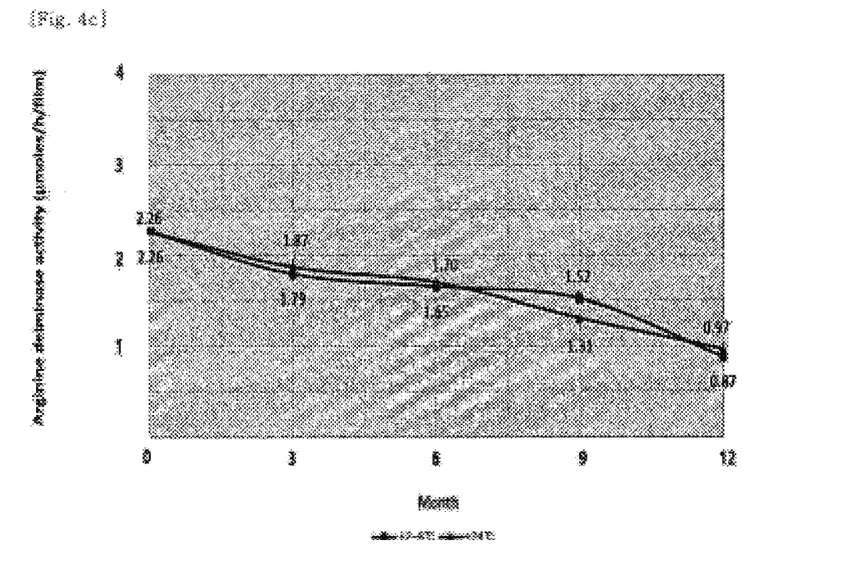

FIG. 4 shows the arginine deiminase activity of the strain *L. brevis* ATCC 4006 monitored during twelve months storage of the films at temperatures of 2-8° C. and +24° C. In all three lots enzyme activity suffered a pharmacologically acceptable decrease at both temperatures. Mean values for enzyme activity found in the buccal films stored at +2-8° C. decreased from 1.72 mols/h/film at time zero to 0.93 fools/h/film after a twelve month storage period. Mean enzyme activity values found in the buccal films stored at +24° C. decreased from 1.95 mols/h/film at time zero to 0.85 μmols/h/film after twelve months storage.

The results shown in FIG. 3 and FIG. 4 demonstrate that the method of producing the films is highly compatible with the vitality of the probiotic(s) and allows the microorganisms and their metabolic activity to be stored satisfactorily over a period of at least 12 months, particularly if under refrigerated conditions. No traces of contamination by fungi and bacteria were found.

Lactobacilli and Bifidobacteria suitable for application on the films according to the invention are: *Lactobacillus acidophilus, Lactobacillus buchneri, Lactobacillus brevis, Lactobacillus casei, Lactobacillus catenaforme, Lactobacillus cellobiosus,* Lacto*bacillus* crispatus, *Lactobacillus curvatus, Lactobacillus delbrueckii, Lactobacillus jensenii, Lactobacillus leichmanii, Lactobacillus minutus, Lactobacillus plantarum Lactobacillus rogosae, Lactobacillus salivarius, Lactobacillus reuteri, Lactobacillus rhamnosus* GG, *Bifidobacterium animalis* subsp. *lactis* BB-12, *Bifidobacterium* adolescentis, *Bifidobacterium angulatum, Bifidobacterium bifidum, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Streptococcus lactis, Streptococcus raffinolactis, Streptococcus thermophilus,* and mixtures thereof. Those preferred, taken individually or as mixtures, are: *Lactobacillus brevis* ATCC 4006, *Lactobacillus salivarius* DSM 24800, *Lactobacillus plantarum* DSM 24801, *Streptococcus thermophilus* DSM 24731, *Lactobacillus acidophilus* DSM 24735, *Lactobacillus* delbrueckii ssp *bulgaricus* DSM 24734, *Lactobacillus paracasei* DSM 24733, Lacto*bacillus plantarum* DSM 24730, *Bifidobacterium longum* DSM 24736, *Bifidobacterium infantis* DSM 24727, *Bifidobacterium breve* DSM 24732. *Lactobacillus brevis* ATCC 4006 is particularly preferred.

The preferred enzymes for application to the films according to the invention, alone or in combination with the lactic bacteria and bifidobacteria listed above, are selected from: acid, neutral and alkaline sphingomyelinases, arginine deiminase, which may also be obtained from non-vital bacteria, for example bacteria which have been lysed with ultrasound or inactivated and lysed using methods not prejudicial to the activities of the enzymes of interest.

The film may also contain or be associated with other active ingredients of synthetic or natural origin, for example substances having a local anaesthetic action, such as, by way of example, lidocaine and prilocaine, anti-inflammatory activity, for example, ketoprofen, ibuprofen, arnica, spirea, mallow, antibiotics such as for example doxycycline, or cosmetic and cosmeceutic products, such as, for example, skin clarifiers. The film may also contain other excipient substances such as taste-correcting substances, for example, essential oils, natural or synthetic flavourings, sweeteners, colourings approved for both food and pharmaceutical use, artificial sweeteners and other substances known to those skilled in the art for the preparation of formulations for buccal use.

In addition to this, the mucoadhesive films according to the invention may be included in a kit in combination with other pharmaceutically, cosmeceutically and dermatologically active ingredients for combined, simultaneous, sequential or delayed administration.

The mucoadhesive films according to the invention may be used in the prevention and cure of conditions and diseases in the mucosa of animals and man, which can be effectively treated with probiotics understood as defined above, and for curative personal hygiene. A particularly preferred probiotic is *Lactobacillus brevis* ATCC 4006. Other preferred probiotics are: *Lactobacillus salivarius* DSM 24800, Lacto*bacillus plantarum* DSM 24801, *Streptococcus thermophilus* DSM 24731, Lacto*bacillus acidophilus* DSM 24735, *Lactobacillus delbrueckii* ssp *bulgaricus* DSM 24734, *Lactobacillus paracasei* DSM 24733, *Lactobacillus plantarum* DSM 24730, *Bifidobacterium longum* DSM 24736, *Bifidobacterium infantis* DSM 24727, *Bifidobacterium breve* DSM 24732.

Particularly preferred are conditions of the oral cavity, such as for example, buccal ulcers of various origins, aphthae and parodontal conditions. Conditions of the gastric, genital, anal, nasal, auricular and cutaneous mucosa, such as, by way of a non-limiting example, vaginitis and vaginosis, procto-haemorrhoidal inflammations, sinusitis, otitis, conjunctivitis, gastritis, oesophagitis, damage to the mucosa, mucosal manifestations of systemic diseases, abrasions, open wounds, skin ulcers and sores, in particular pressure sores, are particularly preferred.

In particular, conditions of the oral cavity are for example dental caries, periodontal disturbances and halitosis, gingivitis, oral mucositis, aphthous stomatitis, ulcers such as oral ulcers present in patients suffering from Behcet's Syndrome, microorganism imbalances in the oral cavity, cell proliferation and inflammatory processes in the mucosa, acute and chronic periodontitis, aggressive periodontitis, gingival bleeding, conditions associated with the growth of Streptococci, in particular belonging to the mutans group, conditions associated with the growth of bacterial species such as *Porphyromonas gingivalis, Treponema denticola, Tannerella forsythia* and *Aggregatibacter actinomycetemcomitans*. The films according to the invention are also useful for alleviating problems in patients receiving chemotherapy treatments giving rise to affections of the mucosa, thus increasing compliance with anti-tumour treatment. Tumours affecting the skin, such as for example, melanoma, are also preferred.

The advantages of the invention may be summarised as:
high probiotic loading, thanks to the use of lyophilised probiotics, in higher concentrations than in comparison with fresh cultures;
simplicity of the production process;
long shelf life, high stability during storage, particularly in the case where bacterial enzyme products are used;
differential distribution on the two surfaces of the film allowing directional release of the enzyme or bacteria and different applications (towards the oral cavity or towards the mucosa);
prolonged residence of the mucoadhesive system in situ;
prolonged/sustained release of the active ingredients;
long hydration times (hygroscopicity/water uptake) sustaining prolonged release;
extremely low weight and thickness of the film, thanks to the formulation strategy, in particular in relation to the method of preparation.

These data suggest that the mucoadhesive films according to the present invention are suitable for prolonged and suitably directionable release towards the oral cavity or gingiva, depending upon the condition requiring treatment, thanks to the presence of probiotic on only one side of the mucoadhesive film.

The mucoadhesive film according to the invention may be used to prepare manufactured articles for pharmaceutical and non-pharmaceutical use, for example, individual throw-away units which may be packed in suitable primary packaging units or units of larger dimensions that can be subsequently divided up using a pair of scissors at the time of application in order to adjust the dimensions of the film to the part onto which the unit will be applied. With the film it is also, for example, possible to prepare strips which are suitably packed and wound to form a tape that can be cut at the time of use.

With the process according to the invention it is possible to obtain highly flexible films of thickness 0.01-2 mm, preferably 0.015-0.2 mm, which fit well on the mucosa, in particular the buccal mucosa.

The following examples are provided with a view to illustrating the invention and are not to be regarded as limiting its scope.

Materials

Hydroxypropylmethylcellulose (HPMC, Methocel K100), polyvinylpyrrolidone K15 (PVP) and propylene glycol (PG) were obtained from Fluka (Milan, Italy). *L. brevis* ATCC 4006 was supplied by Namu (Seoul, Korea) in pure lyophilised form [($10^{11}$ colony-forming units per gram (CFUC/g)]. MRS, Nutrient Agar (NA) and Sabouraud Dextrose Agar (SDA) were obtained from Difco (Becton, Dickinson and Co., Sparks, Md.); Anaerocult A was acquired from Merck KGaA (Darmstadt, Germany). All the other chemicals and solvents were of analytical grade and acquired from Carlo Erba (Milan, Italy). The hydration, mucoadhesion and release studies were carried out in aqueous buffer (33.87 mM $KH_2PO_4$, 46.79 mM $Na_2HPO_4.12H_2O$) raised to pH 6.8 with phosphoric acid.

Example 1: Preparation of an OTF Containing HPMC and Propylene Glycol

Hydroxypropylmethylcellulose (2.5% w/w) and propylene glycol (1%) were dissolved in distilled water, and the solution was stirred for 8 hours. The viscous solution was allowed to stand at ambient temperature overnight to ensure that bubbles disappeared. This solution (6.7 g) was then poured into and uniformly distributed in a Petri dish (diameter 5 cm) and dried at 50° C. for 5 hours. Subsequently the lyophilised powder of *L. brevis* ATCC 4006 was sprayed onto a film surface of 1 cm diameter (12.7 mg/cm$^2$) using glass rings of height 1 cm and diameter 1 cm to delimit the surface area. Finally, the Petri dish was placed in a dryer for 24 hours until the film was of constant weight.

Example 2: Characterisation of the Buccal Films in Example 1

2.1. Film Thickness

Mean thickness (Mitutoyo gauge, Mitutoyo Mfc Co. Ltd, Tokyo, Japan) and mean weight (electronic balance) were determined from an observation of three films for each lot. Uniformity of thickness was evaluated at five points per film in each lot. The results of the measurements performed are shown in Table 1.

TABLE 1

Thickness of three different mucoadhesive films (A, B and C) for each experimental production lot. The data are expressed as the mean of five measurements carried out at randomly selected points on the films ± standard deviation.

|   | Lot I | Lot II | Lot III |
|---|---|---|---|
| A | 88.33 ± 5.29 | 85.28 ± 5.07 | 80.00 ± 5.94 |
| B | 83.07 ± 5.89 | 82.10 ± 5.12 | 86.37 ± 4.02 |
| C | 83.33 ± 6.05 | 84.18 ± 6.44 | 85.29 ± 6.23 |

2.2. Buccal Film Hydration Studies

In vitro hydration studies were carried out in phosphate buffer at pH 6.8 simulating human saliva, measuring weight gain at predetermined times (Abruzzo et al., 2012). The films were weighed and placed on filter paper (diameter 40 mm) soaked with phosphate buffer at pH 6.8 and positioned over a sponge (5 cm×5 cm×2 cm) previously soaked in hydration medium and placed in a Petri dish filled with the same buffer to a depth of 0.5 cm. Water absorption was determined as the weight gain of the film after 6 hours, using the following equation:

$$\% \text{ water absorption}(WU)=(WHip-WHp-WDi)/WDi$$

where WHip is the weight of the hydrated film and wet filter paper, WHp is the weight of the wet filter paper and WDi is the initial weight of the dry film. The measurements were performed on three films for each lot and the results are shown in FIG. 2.

2.3. Determination of Water Content by Thermogravimetric Analysis (TGA)

The water content of the mucoadhesive films according to the invention was measured with the TA Q50 instrument ($\beta$=10 K m$^{-1}$, static air atmosphere, temperature 30-100° C., held constant at 100° C. for 15 minutes) in order to study the water content and evaluate the integrity of the film under different storage conditions. The measurements were made on three films for each lot.

Three lots of film were produced. These lots were stored in dehydrating containers, for example containing anhydrous silica gel, at two different temperatures (+2-8° C. and +24° C.) for six months. Water content was evaluated at different times: time zero (t0), 2 weeks (t1), 4 weeks (t2), 8 weeks (t3), 12 weeks (t4), 24 weeks (t5), 36 weeks (t6) and 48 weeks (t7).

TABLE 2

The values represent the mean of three measurements ± SD per lot

|  | Lot I | | Lot II | | Lot III | |
|---|---|---|---|---|---|---|
|  | +2-8° C. | +24° C. | +2-8° C. | +24° C. | +2-8° C. | +24° C. |
| t0 | 5.34 ± 0.31 | 5.34 ± 0.31 | 4.98 ± 0.24 | 4.98 ± 0.24 | 5.42 ± 0.23 | 5.42 ± 0.23 |
| t1 | 5.75 ± 0.22 | 3.95 ± 0.40 | 4.90 ± 0.26 | 2.57 ± 0.22 | 5.36 ± 0.17 | 3.50 ± 0.27 |
| t2 | 4.56 ± 0.28 | 2.14 ± 0.36 | 3.97 ± 0.31 | 1.81 ± 0.18 | 4.56 ± 0.09 | 3.07 ± 0.18 |
| t3 | 2.98 ± 0.16 | 1.85 ± 0.29 | 3.89 ± 0.15 | 1.50 ± 0.28 | 3.50 ± 0.16 | 2.88 ± 0.10 |
| t4 | 2.18 ± 0.18 | 2.06 ± 0.36 | 2.67 ± 0.22 | 1.47 ± 0.15 | 2.71 ± 0.16 | 1.94 ± 0.21 |

TABLE 2-continued

The values represent the mean of three measurements ± SD per lot

| | Lot I | | Lot II | | Lot III | |
|---|---|---|---|---|---|---|
| | +2-8° C. | +24° C. | +2-8° C. | +24° C. | +2-8° C. | +24° C. |
| t5 | 1.97 ± 0.13 | 1.85 ± 0.22 | 2.25 ± 0.20 | 1.37 ± 0.10 | 2.13 ± 0.17 | 1.84 ± 0.21 |
| t6 | 2.17 ± 0.16 | 2.05 ± 0.25 | 2.41 ± 0.16 | 1.49 ± 0.22 | 2.08 ± 0.27 | 2.07 ± 0.31 |
| t7 | 2.23 ± 0.22 | 1.67 ± 0.35 | 1.39 ± 0.56 | 1.74 ± 0.44 | 2.18 ± 0.42 | 1.75 ± 0.51 |

2.4. In Vivo Study of the Mucoadhesive Properties of the Buccal Films

The mucoadhesion properties of the buccal films were tested on five healthy volunteers aged between 25 and 40. The volunteers were instructed to apply the film to the gingival mucosa above the canine tooth, pressing for 60 s (Perioli et al., 2004) and to abstain from eating or drinking during the course of the test. Before the test, hot drinks (for example, tea, coffee, milk, etc.) were avoided for at least two hours, while food/drinks containing probiotics and antiseptic mouthwashes were avoided for at least one week. The films were observed for 5 hours. The volunteers were monitored to evaluate any irritation of the mucosa and residence time (time required for complete removal of the film).

2.5. Stability Studies 2.5.1. Vitality of *L. brevis* ATCC 4006

The vitality of *L. brevis* ATCC 4006 in the mucoadhesive buccal films stored at 2 8° C. and +24° C. was evaluated at various intervals of time (t0=baseline; t1=2 weeks; t2=4 weeks; t3=8 weeks; t4=12 weeks; t5=24 weeks; t6=36 weeks; t7=48 weeks) as illustrated in FIG. 3.

The buccal films were suspended in 10 mL of phosphate buffer (pH 6.8) containing 0.05% of L-cysteine. Incubation at 37° C. for 24 hours was required for complete dissolution of the film. Serial dilutions in physiological solution were inoculated onto agarised MRS plates containing 0.05% of L-cysteine, which is a selective medium for *Lactobacillus*. All the plates were incubated at 37° C. for 48 hours under anaerobic conditions, using anaerobic jars containing Anaerocult A. In addition to this, in order to evaluate contamination of the film by microorganisms the same serial dilutions were inoculated onto NA and SDA plates to count total bacteria and fungi respectively. All the plates were incubated under anaerobic conditions at 37° C. (NA) and 30° C. (SDA) for 48 hours. The plate counts were carried out in duplicate. The results obtained were converted into logarithmic values and means and standard deviations were calculated.

2.5.2. Preservation of Enzyme Activity

The enzyme activity of *L. brevis* ATCC 4006 in mucoadhesive buccal films stored at 2-8° C. and +24° C. was evaluated at various intervals of time (t0=baseline; t1=2 weeks; t2=4 weeks; t3=8 weeks; t4=12 weeks; t5=24 weeks; t6=36 weeks; t7=48 weeks) as illustrated in FIG. 4.

The buccal film was resuspended in 1 ml of 0.9M NaCl and treated with ultrasound in ice (30 minutes, alternating 1 minute of ultrasound and 1 minute's rest) using a Misonix ultrasound device (untreated bacterial extract obtained from the film). Arginine deiminase activity was measured as described by Zuniga et al. (1998) with some modifications. Briefly, arginine deiminase was assayed in a reaction mixture containing 10 mM of phosphate buffer (pH 7.0), 3 mM of L-arginine and a specific volume of untreated bacterial extract obtained from the film using known procedures present in the cited literature. After incubation for 1 hour at 37° C. the reaction was interrupted through the addition of 12 M HCl. The samples were centrifuged at 11000×g for 20 min. The citrulline resulting from the reaction was determined using the modified Archibald method (Archibald, 1944). 1.5 ml of an acid mixture ($H_2SO_4$—$H_3PO_4$; 1:3, vol/vol) and 0.25 ml of diacetyl monoxime (2,3-butandione monoxime) at 1.5% w/v was added to 1 ml of the centrifuged sample. The mixture so obtained was boiled in the dark for 30 minutes. After cooling for 10 minutes in the dark the absorbance of the samples and standards (free citrulline) prepared in the same way was read at 490 nm. Arginine hydrolysis in the buccal films was expressed as μmol citrulline/h/film and determined by comparison with standard curves obtained using free citrulline.

2.6. In Vivo Release Studies 2.6.1. Release of *L. brevis* ATCC 4006

In vivo release studies for the probiotic were carried out on five healthy volunteers aged between 25 and 40.

In a series of experiments (Table 3) the mucoadhesive films were caused to adhere to the gingival mucosa, as described above, with the side having the probiotic facing the oral cavity. Saliva samples were obtained before applying the film ($t_{0\ h}$), and after 2 hours ($t_{2\ h}$) and 10 hours ($t_{10\ h}$). One ml of saliva was serially diluted to determine the quantity of lactobacilli, as described in the section relating to microbiological analysis.

In other experiments (Table 4) the mucoadhesive films were used with the side having the probiotic facing the gingiva, to study release to the gingival mucosa.

TABLE 3

*Lactobacillus* concentrations in saliva samples taken from healthy volunteers (A, B, C, D, E and F). The mucoadhesive films were applied with the probiotic facing the oral cavity. The counts were carried out before ($t_{0\ h}$) and after ($t_{2\ h}$, $t_{10\ h}$) application of the film, and are expressed as mean of log CFU ± SD.

| | *Lactobacillus* concentration (log CFU/ml ± SD) | | | | |
|---|---|---|---|---|---|
| Time (h) | Volunteer A | Volunteer B | Volunteer C | Volunteer D | Volunteer E |
| $t_{0\ h}$ | 5.00 ± 0.07 | <1 | 1.70 ± 0.11 | 3.43 ± 0.12 | <1 |
| $t_{2\ h}$ | 5.30 ± 0.10 | 1.00 ± 0.06 | 1.70 ± 0.05 | 4.82 ± 0.21 | <1 |
| $t_{10\ h}$ | 5.92 ± 0.12 | 2.30 ± 0.10 | 2.00 ± 0.10 | 6.84 ± 0.25 | 4.00 ± 0.21 |

TABLE 4

Lactobacillus concentration in gingival swabs from healthy volunteers (A, B, C, D, E and F) using hydrophilic cotton swabs. The mucoadhesive films were applied with the probiotic facing the gingiva. Counts were carried out before ($t_{0\,h}$) and after ($t_{10\,h}$) application of the film and are expressed as mean of log CFU ± SD.

| | Lactobacillus concentration (log CFU/ml ± SD) | | | | |
|---|---|---|---|---|---|
| Time (h) | Volunteer A | Volunteer B | Volunteer C | Volunteer D | Volunteer E |
| $t_{0\,h}$ | 3.69 ± 0.09 | <1 | 2.08 ± 0.08 | 3.01 ± 0.12 | <1 |
| $t_{10\,h}$ | 4.84 ± 0.13 | 3.61 ± 0.17 | 3.95 ± 0.11 | 4.64 ± 0.21 | 4.36 ± 0.10 |

Gingival swabs were also obtained before application of the film ($t_{0\,h}$) and after 10 hours ($t_{10\,h}$) following application of the film to the gingiva using the side without probiotic. The swabs were immediately immersed in 2 ml of physiological solution. The physiological solution was then diluted so that the lactobacilli could be counted. The detection limit for lactobacilli in respect of saliva samples and the swabs was 10 CFU/ml (1 log CFU/ml).

2.6.2. Release of the Enzyme Arginine Deiminase

In vivo release studies of the enzyme arginine deiminase were carried out on five healthy volunteers aged between 25 and 40.

The mucoadhesive films were caused to adhere to the gingival mucosa with the side having the probiotic facing the oral cavity. Saliva samples were obtained before application of the film ($t_{0\,h}$) and after 2 hours ($t_{2\,h}$) and 10 hours ($t_{10\,h}$) (Table 5).

Arginine deiminase activity in the saliva samples was measured as described previously in section 2.5.2. Arginine hydrolysis in the saliva samples was expressed as mM of citrulline.

TABLE 5

Arginine deiminase activity in saliva samples from 5 volunteers (A, B, C, D and E). The counts were carried out before ($t_{0\,h}$) and after ($t_{10\,h}$) application of the film with the side having the probiotic towards the oral cavity and were expressed as mean concentration (mM) of citrulline ± SD.
Bacterial arginine deiminase activity expressed as concentration (mM) of citrulline produced

| Time (h) | Volunteer A | Volunteer B | Volunteer C | Volunteer D | Volunteer E |
|---|---|---|---|---|---|
| $t_{0\,h}$ | 2.25 ± 0.08 | 2.33 ± 0.02 | 2.09 ± 0.02 | 1.89 ± 0.05 | 2.66 ± 0.02 |
| $t_{2\,h}$ | 2.59 ± 0.05 | 3.80 ± 0.07 | 2.61 ± 0.06 | 1.74 ± 0.01 | 3.08 ± 0.08 |
| $t_{10\,h}$ | 3.21 ± 0.12 | 2.55 ± 0.11 | 1.75 ± 0.08 | 1.74 ± 0.03 | 2.10 ± 0.06 |

2.7. Morphological Analyses

SEM (scanning electron microscopy) analysis was carried out in order to study the morphological structure of the buccal films. The films were fixed on suitable supports and coated with gold/palladium under an argon atmosphere. The samples were then observed using a LEO 420 microscope (LEO Electron Microscopy Ltd., England) set to 1.5 kV.

2.8. Statistical Analyses

All the experiments were carried out in triplicate. The results are expressed as means±SD. The ANOVA test was used to determine statistical significance. The differences were considered to be significant at values of $p<0.05$.

Example 3: Preparation of an OTF Containing HPMC, PVP and Propylene Glycol

Hydroxypropylmethylcellulose (2.5% w/w), polyvinylpyrrolidone K15 (17.5% w/w) and propylene glycol (8% w/w) were dissolved in distilled water and the solution was stirred for 8 hours. The viscous solution was left overnight at ambient temperature to ensure that the bubbles disappeared. This solution was then poured and uniformly distributed in a Petri dish to obtain a thickness of 0.5 mm and was left to dry at 50° C. for 5 hours. Subsequently lyophilised *L. brevis* ATCC 4006 powder was sprayed onto a film surface of 1 cm diameter (12.7 mg/cm$^2$) using glass rings of height 1 cm and 1 cm diameter to delimit the surface area. Finally the Petri dish was placed in a desiccator for 24 hours until the film weight was constant.

Example 4: Preparation of OTF Containing Other Mucoadhesive Polymers

Example 3 was repeated using the following polymers: sodium alginate, sodium hyaluronate, gum arabic, gelatin and mixtures thereof. Mixtures of the following probiotics were applied to the films: *Lactobacillus salivarius* DSM 24800, Lacto*bacillus plantarum* DSM 24801, *Streptococcus thermophilus* DSM 24731, Lacto*bacillus acidophilus* DSM 24735, *Lactobacillus delbrueckii* ssp *bulgaricus* DSM 24734, *Lactobacillus paracasei* DSM 24733, *Lactobacillus plantarum* DSM 24730, *Bifidobacterium longum* DSM 24736, *Bifidobacterium infantis* DSM 24727, *Bifidobacterium breve* DSM 24732. The probiotic mixtures were applied in concentrations varying from 10 to 15 mg/cm$^2$.

Example 5: Preparation of an OTF Containing HPMC, PVP and Propylene Glycol Using a Spreading Machine Hydroxypropylmethylcellulose (2.0% w/w), polyvinylpyrrolidone K15 (18.0%) and propylene glycol (4.0%) were dissolved in distilled water and the solution was stirred for 8 hours. The viscous solution was left overnight at ambient temperature to ensure that bubbles disappeared. This solution was then spread using a Mathis LTE-S(M) spreading machine (Mathis, Oberhasli, Switzerland)

equipped with a suitable scraper. Spreading was onto a silicone substrate in a thickness of 500 micron. The solution spread in this way was then dried (the spreading machine was provided with a heated channel) with forced circulation at 50° C. for 4 minutes. Subsequently the lyophilise *L. brevis* ATCC 4006 powder was sprayed onto a surface of 1 cm diameter (12.7 mg/cm$^2$) using glass rings of height 1 cm and 1 cm diameter to delimit the surface area. The film was then further dried using forced circulation at a temperature of <40° C. for 8 minutes. Finally the film was cut and packed in individual units in sachets impermeable to moisture and oxygen.

The invention claimed is:

1. A method for the preparation of a bi-layered, stable, dehydrated mucoadhesive film having a surface layer of dehydrated lactic acid bacteria or bifidobacteria, or an enzyme derived from said lactic bacteria or bifidobacteria, or mixtures thereof, the method comprising:
(a) Mixing a mucoadhesive polymer with water and a plasticizing substance in a quantity from between about 0% to 5% w/w based on the weight of the mucoadhesive polymer, thereby making a mixture;
(b) Pouring the mixture onto a surface to form a substantially uniform thickness and drying at a temperature of about greater than or equal to about 30° C., thereby generating a dehydrated mucoadhesive film having a surface,
(c) depositing and distributing an aliquot of the lactic acid bacteria or bifidobacteria bacteria, or the enzyme derived from said lactic bacteria or bifidobacteria, or mixtures thereof, in dehydrated form onto the dehydrated mucoadhesive film surface, thereby generating a bi-layered dehydrated mucoadhesive film comprising a surface layer of dehydrated lactic acid bacteria or bifidobacteria bacteria, or the enzyme derived from said lactic bacteria or bifidobacteria or mixtures thereof; and
(d) drying the mucoadhesive film surface until the bi-layered dehydrated mucoadhesive film reaches a constant weight, thereby producing a stable, dehydrated bi-layered mucoadhesive film.

2. The method of claim 1, in which the mucoadhesive film has a thickness of less than or equal to 1 mm.

3. The method of claim 1, wherein the one or more bacterial strains of lactic bacteria or the one or more bifidobacteria are selected from the group consisting of: *Lactobacillus acidophilus, Lactobacillus buchneri, Lactobacillus brevis, Lactobacillus casei, Lactobacillus catenaforme, Lactobacillus cellobiosus, Lactobacillus crispatus, Lactobacillus curvatus, Lactobacillus delbrueckii, Lactobacillus jensenii, Lactobacillus leichmanii, Lactobacillus minutus, Lactobacillus plantarum Lactobacillus rogosae, Lactobacillus salivarius, Lactobacillus reuteri, Lactobacillus rhamnosus* GG, *Bifidobacterium animalis* subsp. *lactis* BB-12, *Bifidobacterium adolescentis, Bifidobacterium angulatum, Bifidobacterium bifidum, Bifidobacterium catenulatum, Bifidobacterium dentium, Bifidobacterium eriksonii, Bifidobacterium infantis, Bifidobacterium longum, Bifidobacterium plantarum, Bifidobacterium pseudocatenulatum, Bifidobacterium pseudolongum, Streptococcus lactis, Streptococcus raffinolactis, Streptococcus thermophilus*, and mixtures thereof.

4. The method of claim 1, wherein the one or more bacterial strains of lactic bacteria or the one or more bifidobacteria are selected from the group consisting of: *Lactobacillus brevis* ATCC 4006, *Lactobacillus salivarius* DSM 24800, *Lactobacillus plantarum* DSM 24801, *Streptococcus thermophilus* DSM 24731, *Lactobacillus acidophilus* DSM 24735, *Lactobacillus delbrueckii* ssp *bulgaricus* DSM 24734, *Lactobacillus paracasei* DSM 24733, *Lactobacillus plantarum* DSM 24730, *Bifidobacterium longum* DSM 24736, *Bifidobacterium infantis* DSM 24727, *Bifidobacterium breve* DSM 24732 and mixtures thereof.

5. The method of claim 1, wherein the mucoadhesive film is obtained or derived from a homo- or co-polymerizable monomer selected from the group consisting of:
hydroxyethyl methacrylate (HEMA);
hydroxyethoxyethyl methacrylate (HEEMA);
hydroxydiethoxyethyl methacrylate (HDEEMA);
methoxyethyl methacrylate (MEMA);
methoxyethoxyethyl methacrylate (MEEMA);
methoxydiethoxyethyl methacrylate (MDEEMA);
ethylene glycol dimethacrylate (EGDMA);
N-vinyl-2-pyrrolidone (NVP);
N-isopropyl AAm (NIPAAm);
vinyl acetate (VAc);
lactic acid (LA);
acrylic acid (AA);
methacrylic acid (MAA);
N-(2-hydroxypropyl) methacrylamide (HPMA);
ethylene glycol (EG);
propylene glycol (PG);
PEG acrylate (PEGA);
PEG methacrylate (PEGMA);
PEG diacrylate (PEGDA);
PEG dimethacrylate (PEGDMA);
a polymer comprising sodium alginate or a hyaluronic acid;
a polymer comprising ethylene or propylene oxide,
a polymer comprising a beta-glucan, where optionally the beta-glucan comprises pullulan (beta-1,4- or beta-1,6-glucan);
polyvinyl pyrrolidone;
polyvinyl alcohol;
sodium alginate;
sodium hyaluronate
polyethylene glycol;
a gum;
polyacrylic acid;
a polymer comprising acrylic, methacrylic acid, a carboxyvinyl polymer, a starch, a natural or a synthetic gelatin, agarose gel, a polysaccharide, a glucan, a xanthan, an agarose-xanthan gel, a chitosan, a dextran, a pectin, a cellulose; and
mixtures and combinations thereof.

6. The method of claim 5, wherein the cellulose comprises: a methyl-, ethyl-, or propyl-cellulose, carboxymethylcellulose, hydroxypropyl-methylcellulose, hydroxyethylcellulose, or hydroxypropylcellulose.

7. The method of claim 5, wherein the gum comprises xanthan gum, gum adragant, guar gum, or acacia gum.

8. The method of claim 1, wherein the plasticizing substance comprises a composition selected from the group consisting of: a polyalkylene oxide and a small organic molecule having plasticizing properties.

9. The method of claim 8, wherein the polyalkylene oxides comprise polyethylene glycol or polypropylene glycol.

10. The method of claim 8, wherein the plasticizing substance comprises one plasticizing substance or a mixture of plasticizing substances.

11. The method of claim 8, wherein the small organic molecule comprises glycerol, glycerol monoacetate, triacetin, polysorbate, cetyl alcohol, sorbitol, propylene glycol, polyethylene glycol (PEG), or any combination thereof.

12. The method of claim 1, wherein the mixture is poured on to a surface of an article of manufacture.

13. The method of claim 7, wherein the article of manufacture is fabricated for use in a medical, a cosmetic or a non-medical field for an animal or a human.

14. The method of claim 13, wherein the article of manufacture is fabricated for use in a dermatological field or a hygiene field or a personal curative field, or the article of manufacture is fabricated for use on an animal or a human.

15. The method of claim 14, wherein the article of manufacture is formulated for cosmetic use as a skin clarifier.

16. The method of claim 13, wherein the article of manufacture is fabricated for use in a medical field related to a condition or a disease affecting mucosa in general.

17. The method of claim 16, wherein the article of manufacture is fabricated for use for a condition or disease is selected from the group consisting of: oral, genital, anal, nasal, pharyngeal, oesophageal and conjunctival mucosa and the skin of an animal or a human which benefits from the administration of lactic bacteria and bifidobacterial.

18. The method of claim 16, wherein the article of manufacture is fabricated or formulated for use in the prevention or treatment of a mucosal or a skin condition selected from the group consisting of: vaginitis and vaginosis, procto-haemorrhoidal inflammations, sinusitis, otitis, conjunctivitis, gastritis, oesophagitis, injuries to the mucosa, mucosal manifestations of systemic diseases, abrasions, open wounds, skin ulcers, sores, conditions of the mucosa of the oral cavity; a tumor affecting the skin, optionally melanoma, and to increase compliance in patients treated with chemotherapy, optionally for chemotherapy giving rise to problems in the mucosa.

19. The method of claim 18, wherein the article of manufacture is fabricated for use in a disease or a condition of the mucosa of the oral cavity.

20. The method of claim 19, wherein a condition or disease of the oral cavity comprise: a gingival disturbance, dental caries, a periodontal disturbance, halitosis, gingivitis, oral mucositis, an ulcer, a microorganism imbalance in the oral cavity, cell proliferation, an inflammatory process in the mucosa, an acute or a chronic periodontitis, an aggressive periodontitis, gingival bleeding, a condition associated with the growth of Streptococci or *Streptococcal mutans*, a condition associated with the growth of a bacterial species, gastritis, oesophagitis, mucositis or aphthous stomatitis.

21. The method of claim 20, wherein the bacterial species comprise: *Porphyromonas gingivalis, Treponema denticola, Tannerella forsythia* and/or *Aggregatibacter actinomycetemcomitans*.

22. The method of claim 20, wherein the ulcer comprises an oral ulcer in a patient suffering from Behcet's syndrome.

23. The method of claim 1, wherein at least one pharmaceutically, cosmeceutically and dermatologically active ingredient for simultaneous, sequential or delayed administration is added to the mixture or the dehydrated mucoadhesive film surface.

24. The method of claim 1, wherein the enzyme is arginine deiminase.

25. The method of claim 1, wherein the enzymes are obtained or derived from said one or more bacterial strains of lactic bacteria or one or more bifidobacteria are selected from the group consisting of: acid sphingomyelinase, neutral sphingomyelinase and alkaline sphingomyelinase.

26. The method of claim 1, wherein the quantity of the one or more bacterial strains of lactic bacteria and the one or more bifidobacteria on the film's surface is between about $10^2$ and $10^{12}$ cfu/cm$^2$.

27. The method of claim 1, wherein the depositing and distributing an aliquot of the lactic acid bacteria and bifidobacteria bacteria, or the enzyme derived from said lactic bacteria or bifidobacteria or mixtures thereof, in dehydrated form onto the dehydrated mucoadhesive film surface, comprises use of spraying.

* * * * *

UNITED STATES PATENT AND TRADEMARK OFFICE
CERTIFICATE OF CORRECTION

PATENT NO. : 11,065,200 B2
APPLICATION NO. : 16/494148
DATED : July 20, 2021
INVENTOR(S) : Kim et al.

It is certified that error appears in the above-identified patent and that said Letters Patent is hereby corrected as shown below:

On the Title Page

Item (12) delete "Kim" and insert -- Kim et al. --

Item (72) Inventor: please insert the following:
-- Seok-Jin KIM, Seoul, Korea
Barbara LUPPI, Bologna, Italy
Beatrice VITALI, Bologna, Italy
Angela ABRUZZO, Bologna, Italy --

Signed and Sealed this
Eleventh Day of June, 2024

Katherine Kelly Vidal
*Director of the United States Patent and Trademark Office*